United States Patent

Yamamoto et al.

[11] Patent Number: 5,811,591
[45] Date of Patent: Sep. 22, 1998

[54] PROCESS OF PRODUCING HYDROXYALKANAL

[75] Inventors: Hiroshi Yamamoto; Hisakazu Shindou, both of Suita; Hirokazu Itoh, Kobe; Tadahiro Yoneda, Ibaragi; Masatoshi Yoshida, Nara, all of Japan

[73] Assignee: Nippon Shokubai Co., Ltd., Osaka, Japan

[21] Appl. No.: 561,179

[22] Filed: Nov. 20, 1995

[30] Foreign Application Priority Data

Nov. 22, 1994 [JP] Japan ..................................... 6-288315
Apr. 7, 1995 [JP] Japan ..................................... 7-082976
Apr. 7, 1995 [JP] Japan ..................................... 7-082977

[51] Int. Cl.$^6$ .................................................... C07C 45/61
[52] U.S. Cl. ............................ 568/491; 568/465; 568/862
[58] Field of Search ..................................... 568/465, 862, 568/491

[56] References Cited

U.S. PATENT DOCUMENTS

| | | | |
|---|---|---|---|
| 2,434,110 | 1/1948 | Hatch et al. | 260/602 |
| 3,536,763 | 10/1970 | Eleuterio et al. | 260/602 |
| 5,015,789 | 5/1991 | Arntz et al. | 568/862 |
| 5,093,537 | 3/1992 | Unruh et al. | 568/862 |
| 5,171,898 | 12/1992 | Arntz et al. | 568/862 |
| 5,276,201 | 1/1994 | Haas et al. | 568/491 |
| 5,284,979 | 2/1994 | Haas et al. | 568/491 |

Primary Examiner—Gary Geist
Assistant Examiner—Sreeni Padmanabhan
Attorney, Agent, or Firm—Kubovcik & Kubovcik

[57] ABSTRACT

An unsaturated aldehyde expressed by Formula (I) below is hydrated with a solution in the presence of a carboxylic-acid-based resin having of a structure expressed by Formula (II) below:

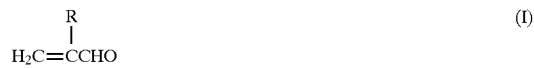

where R represents one of a hydrogen atom and a hydrocarbon group having up to five carbons;

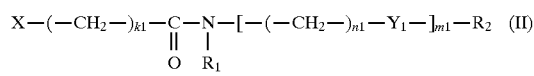

where $R_1$ and $R_2$ respectively represent a hydrogen atom, hydrocarbon group having up to five carbons, or —($-CH_2-$)$_{p1}$—X group, $p_1$, $k_1$, and $m_1$ respectively represent an integer from zero to six, $n_1$ represents an integer from one to six, $Y_1$ represents —O—, —S—, or —NR$_3$—, $R_3$ represents a hydrogen atom or hydrocarbon group having up to five carbons, and X represents a carboxylic-acid-based resin main body. Using a heat-resistant catalyst as above makest it possible to increase the reaction rate by heating, and produce hydroxyalkanal at high selectivity and yield out of an industrially advantageous high-concentration unsaturated aldehyde solution.

57 Claims, No Drawings

PROCESS OF PRODUCING HYDROXYALKANAL

FIELD OF THE INVENTION

The present invention relates to a process of producing hydroxyalkanal by hydrating an unsaturated aldehyde in an aqueous solution in the presence of a catalyst.

BACKGROUND OF THE INVENTION

In conventional processes, an unsaturated aldehyde, namely, acrolein, is hydrated with a solution in the presence of a catalyst to obtain hydroxyalkanal, namely, 3-hydroxypropanal(3-hydroxypropionaldehyde), which will be explained in the following paragraphs.

U.S. Pat. No. 2,434,110 discloses a process, in which a mineral acid, such as a sulfuric acid, is used as a homogeneous acid catalyst for the above reaction step. However, 3-hydroxypropanal retains low selectivity in this process, and thus is not produced efficiently. In addition, neither is 3-hydroxypropanal readily separated from the homogeneous catalyst, nor can the catalyst be re-used easily.

To eliminate such a drawback, processes for improving the selectivity of 3-hydroxypropanal are proposed in the undermentioned publications. U.S. Pat. No. 3,536,763 discloses a process, in which an acid ion exchange resin is used as an heterogeneous acid catalyst for the above reaction step. U.S. Pat. No. 5,015,789 and U.S. Pat. No. 5,171,898 disclose processes, in which an ion exchange resin containing a phosphonate group, an amino group, or an aminophosphate group is used as a heterogeneous acid catalyst for the above reaction step. U.S. Pat. No. 5,093,537 discloses a process, in which alumina bonding zeolite is used as a heterogeneous acid catalyst for the above reaction step. U.S. Pat. No. 5,276,201 discloses a process, in which $TiO_2$ carrying a phosphoric acid is used as a heterogeneous acid catalyst for the above reaction step. Also, U.S. Pat. No. 5,284,979 discloses a process, in which the above reaction step is performed using a buffer solution containing a carboxylic acid and tertiary amine in the presence of an acid catalyst.

If a resulting solution of the raw material, acrolein, has low concentration (i.e., lower than 20 percent by weight), 3-hydroxypropanal retains satisfactory selectivity, thereby making it possible to obtain 3-hydroxypropanal at high selectivity by the above processes.

However, the inventors of the present invention found that when an industrially advantageous high-concentration acrolein solution (i.e., 20 or more percent by weight) is used for the reaction in each of the above processes, a reaction product, 3-hydroxypropanal, triggers an active consecutive reaction (side reaction) because it has an aldehyde group. In other words, the above processes have a drawback that the selectivity from acrolein to 3-hydroxypropanal, and hence the selectivity of 3-hydroxypropanal is reduced as the concentration of the solution increases.

In addition, the heterogeneous acid catalysts used in the above conventional processes have poor resistance to heat. Thus, if a reaction temperature is raised (over 65° C.) to accelerate the hydration reaction, the heterogeneous acid catalysts are deactivated, thereby reducing the selectivity of 3-hydroxypropanal. Further, although the reason why is not apparent, the metal-carrying heterogeneous acid catalysts used in the above conventional processes retain a low reaction rate in hydration, thereby reducing an industrially advantageous short-time conversion of acrolein.

Therefore, these processes are not industrially satisfactory, because not only is the conversion of acrolein low, but also the reaction rate can not be increased by heating, besides the yield of 3-hydroxypropanal can not be improved by increasing the concentration of the acrolein solution.

SUMMARY OF THE INVENTION

It is therefore an object of the present invention to provide a process of producing hydroxyalkanal capable of (1) increasing a reaction rate by heating while improving an industrially advantageous short-time conversion of an unsaturated aldehyde with the use of a heat-resistant catalyst, and (2) producing hydroxyalkanal at high yield and selectivity out of an industrially advantageous high-concentration unsaturated aldehyde solution.

To fulfil the above object, the inventors of the present invention performed experiments of processes for producing hydroxyalkanal by hydrating an unsaturated aldehyde in an aqueous solution in the presence of a catalyst, and found that the selectivity from an unsaturated aldehyde to hydroxyalkanal and the yield of hydroxyalkanal were improved when the catalyst was a carboxylic-acid-based resin having a substitutional group of a specific structure, and/or a carboxylic-acid-based resin made of a copolymer of an unsaturated monomer (A) containing a carboxyl group with an unsaturated monomer (B) containing an amino group and/or an amide group. It was also acknowledged that the carboxylic-acid-based resin serving as the catalyst retained excellent heat resistance and the reaction temperature could be raised, thereby making it possible to increase the reaction rate by heating. In other words, the gist of the present invention is to use a heat-resistant carboxylic-acid-based resin as a catalyst, and the effects are that (1) the reaction rate can be raised by heating, and (2) hydroxyalkanal can be produced at high selectivity and yield out of an industrially advantageous high-concentration unsaturated aldehyde solution.

The inventors of the present invention also found that the reaction rate of the hydration was increased and the selectivity from an unsaturated aldehyde to hydroxyalkanal and the yield of hydroxyalkanal were also improved when the catalyst was a metal-carrying ion exchange resin. In other words, the gist of the present invention is to use a metal-carrying carrying ion exchange resin as a catalyst, and the effects are that (1) an industrially advantageous short-time conversion of an unsaturated aldehyde is improved, and (2) hydroxyalkanal can be produced at high selectivity and yield out of an industrially advantageous high-concentration unsaturated aldehyde solution.

To fulfill the above object, a process of producing hydroxyalkanal in accordance with the present invention is characterized by comprising a step of hydrating an unsaturated aldehyde expressed by Formula (I) below in an aqueous solution in the presence of a carboxylic-acid-based resin having at least one structure selected from a group consisting of structures expressed by Formulas (II), (III), (IV), (V), and (VI) below:

where R represents a hydrogen atom or hydrocarbon group having up to five carbons;

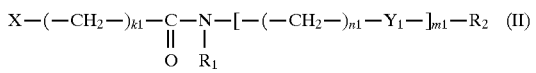

where $R_1$ and $R_2$ respectively represent a hydrogen atom, hydrocarbon group having up to five carbons, or $-(-CH_2-)_{p1}-X$ group, $p_1$, $k_1$, and $m_1$ respectively represent an zero or an integer from one to six, $n_1$ represents an integer from one to six, $Y_1$ represents $-O-$, $-S-$, or $-NR_3-$, $R_3$ represents a hydrogen atom or hydrocarbon group having up to five carbons, and X represents a carboxylic-acid-based resin main body;

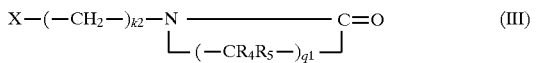

where $R_4$ and $R_5$ respectively represent a hydrogen atom or hydrocarbon group having up to five carbons, $k_2$ represents an integer from one to six, $q_1$ represents zero or an integer from three to six, and X represents a carboxylic-acid-based resin main body;

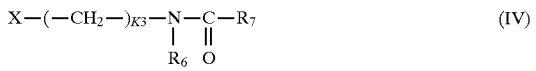

where $R_6$ represents a hydrogen atom, hydrocarbon group having up to five carbons, or $-(-CH_2-)_{p2}-X$ group, $p_2$ represents zero or an integer from one to six, $R_7$ represents a hydrocarbon group having up to five carbons or $-(-CH_2-)_{p3}-X$ group, $p_3$ and $k_3$ respectively represent an integer from zero to six, and X represents a carboxylic-acid-based resin main body;

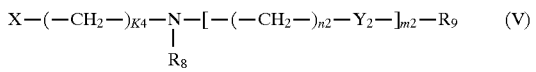

where $R_8$ represents a hydrogen atom, hydrocarbon group having up to five carbons, or $-(-CH_2-)_{p4}-X$ group, $p_4$ and $k_4$ respectively represent zero or an integer from one to six, $n_2$ represents an integer from one to six, Y2 represents $-O-$, $-S-$, $-NR_{10}-$, or $-CH_2-$, $R_{10}$ represents a hydrogen atom or hydrocarbon group having up to five carbons, and X represents a carboxylic-acid-based resin main body, $m_2$ represents zero or an integer from one to six, $R_9$, when $m_2 \neq 0$, represents a hydrogen atom, hydrocarbon group having up to five carbons, $-(-CH_2-)_{p5}-X$ group, or Brønsted acid residue and, when $m_2=0$, a hydrogen atom, hydrocarbon group having up to five carbons, or $-(-CH_2-)_{p5}-X$ group, and $p_5$ represents an integer from zero to six;

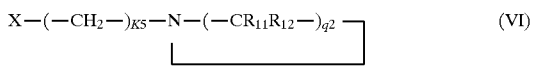

where $R_{11}$ and $R_{12}$ respectively represent a hydrogen atom or hydrocarbon group having up to five carbons, $k_5$ represents zero or an integer from one to six, $q_2$ represents an integer from four to seven, and X represents a carboxylic-acid-based resin main body.

According to the above process, not only a reaction rate can be increased by heating, but also the consecutive reaction (side reaction) of the reaction product, namely, hydroxyalkanal, is curbed, thereby making it possible to produce hydroxyalkanal at high selectivity and yield out of a high-concentration unsaturated aldehyde solution. That is to say, using a heat-resistant carboxylic-acid-based resin can increase the reaction rate by heating and trigger a reaction of an industrially advantageous high-concentration unsaturated aldehyde solution, thereby improving the yield of hydroxyalkanal.

To fulfill the above object, a process of producing hydroxyalkanal in accordance with the present invention is characterized by comprising a step of hydrating an unsaturated aldehyde expressed by Formula (I) in an aqueous solution in the presence of a metal-carrying ion exchange resin.

According to the above process, not only a reaction rate can be increased, but also the consecutive reaction (side reaction) of the reaction product, namely, hydroxyalkanal, is curbed, thereby making it possible to produce hydroxyalkanal at high selectivity and yield out of a high-concentration unsaturated aldehyde solution. That is to say, using a metal-carrying ion exchange resin can improve an industrially advantageous short-time conversion of an unsaturated aldehyde, and trigger a reaction of a high-concentration unsaturated aldehyde solution, thereby improving the yield of hydroxyalkanal.

Other objects and advantages of the present invention will become apparent from the detailed description to follow taken in conjunction with the appended claims.

DESCRIPTION OF THE EMBODIMENT

The raw material of the present invention, namely, an unsaturated aldehyde (2-alkenal) expressed by Formula (I) mentioned above, is not especially limited. In Formula (I), however, a substitutional group represented by R is a hydrogen atom or hydrocarbon group having up to five carbons, and the hydrocarbon group referred to herein is a methyl group, ethyl group, propyl group, butyl group, or amyl group. Examples of the unsaturated aldehyde are: acrolein, methacrolein, 2-formyl-1-butene, 2-formyl-1-pentene, 2-formyl-1-hexene, 2-formyl-1-heptene, and the like. Of all these examples, a preferable unsaturated aldehyde is acrolein.

According to the process in accordance with the present invention, either 2-hydroxyalkanal or 3-hydroxyalkanal is selectively obtained from these examples. More precisely, in case of acrolein whose substitutional group represented by R in Formula (I) is a hydrogen atom, 3-hydroxyalkanal, namely, 3-hydroxypropanal (3-hydroxypropionaldehyde) is selectively obtained. In case of an unsaturated aldehyde whose substitutional group represented by R in Formula (I) is a hydrocarbon group, 2-hydroxyalkanal is selectively obtained. Note that 3-hydroxypropanal, obtained when acrolein is used as the unsaturated aldehyde, is an industrially important raw material of 1,3-propanediol.

The density of an unsaturated aldehyde solution (hereinafter referred to as the density) is, although it depends on unsaturated aldehyde's solubility to water, reaction temperature, etc., preferably in a range between 5 percent by weight and saturation, more preferably in a range between 5 percent by weight and 50 percent by weight, further preferably in a range between 20 percent by weight and 50 percent by weight, and most preferably in a range between 25 percent by weight and 40 percent by weight. The density lower than 5 percent by weight is not preferable because the yield of hydroxyalkanal is reduced. The density exceeding the saturation is also not preferable because an undissolved unsaturated aldehyde triggers a polymerization reaction or the like, and thus reduces the selectivity to hydroxyalkanal.

The catalyst used in the present invention may be, but is not limited to:

(1) a carboxylic-acid-based resin having at least one structure selected from a group consisting of structures represented by Formulas (II), (III), (IV), (V), and (VI) mentioned above;

(2) a carboxylic-acid-based resin made of a copolymer of an unsaturated monomer (A) containing a carboxyl group with an unsaturated monomer (B) containing an amino and/or an amide group; or (3) a metal-carrying ion exchange resin.

In short, the catalyst used in the present invention is (1) a carboxylic-acid-based resin having at least one structure selected from a group consisting of structures expressed by Formulas (II) through (VI), (2) a carboxylic-acid-based resin made of a copolymer of the unsaturated monomer (A) with the unsaturated monomer (B), or (3) a metal-carrying ion exchange resin. One or more than one of these catalysts are used. Note that in the Formulas, X represents a carboxylic-acid-based resin main body, and a carboxylic-acid-based resin is a polymer containing a number of free carboxyl groups. Also, a hydrocarbon group having up to five carbons referred in Formulas (II) through (VI) is a methyl group, ethyl group, propyl group, butyl group, or amyl group.

A carboxylic-acid-based resin containing an amide group (substitutional group) having a structure expressed by Formula (II), (III), or (IV) and a carboxylic-acid-based resin containing an amino group (substitutional group) having a structure expressed by Formula (V) or (VI) are not especially limited. The carboxylic-acid-based resin main body may be a homopolymer of monomers (hereinafter referred to as comonomer for the explanation's convenience) containing a carboxyl group or a copolymer of a monomer containing a carboxyl group with another monomer which can copolymerized with the aforementioned monomer containing a carboxyl group.

The monomer containing a carboxyl group includes, but is not limited to, a carboxylic acid, such as a (meta) acrylic acid, a maleic acid, and a fumaric acid. One or more than one of these monomers are used as occasion demands.

The comonomer may be, but is not limited to, a monomer including an olefin group. Examples of the comonomer are: ester of the above-mentioned monomer containing a carboxyl group, styrene, vinylpyridine, and the like. The comonomer may also contain a functional group other than the carboxyl group, such as a phosphate group, a sulfonate group, hydroxyl group, or the like. One or more than one of these comonomers are used.

Of all the carboxylic-acid-based resins including an amide group having a structure expressed by Formula (II), a carboxylic-acid-based resin whose bivalent substitutional group represented by $Y_1$ includes either a nitrogen atom or sulfur atom is preferable, and the one whose $Y_1$ includes a sulfur atom is particularly preferable in terms of catalytic reactivity. Also, of all the carboxylic-acid-based resins including an amide group having a structure expressed by Formula (III), a carboxylic-acid-based resin having an amide group represented by $q_1$ whose cyclic unit is three is preferable in terms of catalytic reactivity.

Further, of all the carboxylic-acid-based resins including an amino group having a structure expressed by Formula (V), a carboxylic-acid-based resin whose bivalent substitutional group represented by $Y_2$ includes either a nitrogen atom or sulfur atom is preferable, and the one whose $Y_2$ includes a sulfur atom is particularly preferable in terms of catalytic reactivity. A Brønsted acid residue group referred in Formula (V) includes a group liberating a proton, such as a carboxyl group, a phosphate group, a phosphite group, a sulfonate group, and a hydroxyl group. Note that the Brønsted acid residue group referred in the present invention includes a hydrocarbon group having up to five carbons and at least one hydrogen atom substituted by the above group liberating a proton.

A preferred carboxylic-acid-based resin (main body) is a (meta)acrylic-acid-based resin, and when the (meta)acrylic-acid-based resin includes an amide group, a (meta)acrylic acid-(meta)acrylamides copolymer and a (meta)acrylic acid-vinylpyrrolidones polymer are preferable. The (meta)acrylic acid-(meta)acrylamides copolymer includes, but is not limited to, a (meta)acrylic acid-(meta)acrylamide copolymer, a (meta)acrylic acid-N,N-dimethyl(meta)acrylamide copolymer, a (meta)acrylic acid-N-isopropyl(meta)acrylamide copolymer, a (meta)acrylic acid-N,N-dimethylaminopropyl(meta)acrylamide copolymer, and the like. The (meta)acrylic acid-vinylpyrrolidones polymer includes, but is not limited to, an acrylic acid-N-vinylpyrrolidones copolymer.

Also, the (meta)acrylic-acid-based resin having an amino group includes, but is not limited to, a (meta)acrylic acid-2-vinylpyridines copolymer, a (meta)acrylic acid-4-vinylpyridines copolymer, a (meta)acrylic acid-N-vinylcarbazoles copolymer, a (meta)acrylic acid-N-monoarylamines copolymer, a (meta)acrylic acid-N,N-diarylamines copolymer, a (meta)acrylic acid-N,N,N-triarylamines copolymer, a (meta)acrylic acid-4-(N,N-dialkylamino)alkylstyrenes copolymer, and the like.

The carboxylic-acid-based resin made of a copolymer of the unsaturated monomer (A) with the unsaturated monomer (B) is not especially limited. The unsaturated monomer (A) includes, but is not limited to, the above-mentioned monomer containing a carboxyl group.

Of all the unsaturated monomers (B), an unsaturated monomer (B) containing an amino group includes, but is not limited to, nitrogen containing unsaturated compounds, such as vinylpyridines, N-vinylcarbazoles, N-monoarylamines, N,N-diarylamines, N,N,N-triarylamines, 4-(N,N-dialkylamino)alkylstyrenes, 6-(N-propenylamino)-4-thiahexanoic acid, and 6-(N,N-dipropenylamino)-4-thiahexanoic acid.

A substitutional group expressed by Formula (VII) below may bond to a nitrogen atom composing the amino group and/or amide group of the unsaturated monomer (B).

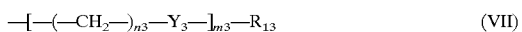

where $n_3$ represents an integer from one to six, $Y_3$ represents —O—, —S—, —$NR_{14}$—, or —$CH_2$—, $R_{14}$ represents a hydrogen atom or hydrocarbon having up to five carbons, $m_3$ represents an integer from zero to six, $R_{13}$, when $m_3 \neq 0$, represents a hydrogen atom, hydrocarbon group having up to five carbons, or Brønsted acid residue and, when m=0, a hydrogen atom or hydrocarbon group having up to five carbons. Further, a carboxylic-acid-based resin may be a copolymer of the unsaturated monomer (A) with the unsaturated monomer (B) and the above-mentioned comonomer. Note that a Brønsted acid residue referred in Formula (VII) is a group liberating a proton such as a carboxyl group, phosphate group, a phosphite group, sulfonate group, and hydroxyl group. Note that the Brønsted acid residue group referred in the present invention includes a hydrocarbon group having up to five carbons and at least one hydrogen atom substituted by the above group liberating a proton.

The vinylpyridines includes, but are not limited to, 2-vinylpyridines, 4-vinylpyridines, and the like. An example of 4-(N,N-dialkylamino)alkylstyrenes is a compound expressed by Formula (VIII):

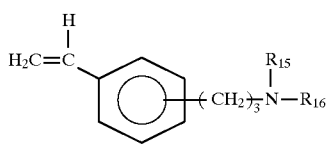

where $R_{15}$ and $R_{16}$ respectively represent a hydrogen atom or hydrocarbon group having up to five carbons and j represents an integer from one to five. The hydrocarbon group having up to five carbons is a methyl group, ethyl group, propyl group, butyl group, or amyl group. Of all the 4-(N,N-dialkylamino)alkylstyrenes expressed by Formula (VIII), 4-(N,N-dialkylamino)alkylstyrenes whose cyclic unit represented by j is from one to three is preferable in terms of reactivity with the unsaturated monomer (A) or catalytic reactivity of a resulting carboxylic-acid-based resin. An example of the 4-(N,N-dialkylamino)alkylstyrenes expressed as Formula (VIII) is 4-(N,N-dimethylamino) ethylstyrene, and the like.

One or more than one of these carboxylic-acid-based resins are used as occasion demands. Note that a process of producing the carboxylic-acid-based resin is not especially limited.

Although it depends on the kinds of the unsaturated aldehyde, reaction conditions, etc., the ratio of the number of nitrogen containing groups and the number of carboxyl groups of a carboxylic-acid-based resin (the number of the nitrogen containing groups/the number of carboxyl groups) is preferably in a range between 1/1000 and 1/1, more preferably in a range between 1/100 and 1/1.5(2/3), and most preferably in a range between 1/20 and 1/2. The nitrogen containing group referred herein is an amide group having a structure expressed by Formula (II), (III), or (IV), an amino group having a structure expressed by Formula (V) or (VI), an amino group residue or amide group residue derived from the unsaturated monomer (B). Neither a ratio smaller than 1/1000 nor a ratio greater than 1/1 is preferable, because the consecutive reaction (side reaction) of the reaction product, namely, hydroxyalkanal, can not be curbed.

When the carboxylic-acid-based resin is a (meta)acrylic acid-vinylpyridines copolymer, for example, an amount of vinylpyridine in the copolymer is determined in a range between 0.1 percent by mole and 50 percent by mole depending on the kinds of the unsaturated aldehyde, reaction conditions, etc. When the carboxylic-acid-based resin is a (meta)acrylic acid-(meta)acrylamides copolymer, an amount of (meta)acrylamide in the copolymer is determined in a range between 0.1 percent by mole and 50 percent by mole depending on the kinds of the unsaturated aldehyde, reaction conditions, etc. Further, when the carboxylic-acid-based resin is a (meta)acrylic acid-vinylpyrolidones copolymer, an amount of a vinylpyrolidone in the copolymer is determined in a range between 0.1 percent by mole and 50 percent by mole depending on the kinds of the unsaturated aldehyde, reaction conditions, etc.

A metal-carrying carboxylic-acid-based resin is preferable to obtain hydroxyalkanal at high selectivity and yield. Metal referred to herein includes, but is not limited to, copper, lead, nickel, zinc, iron, cobalt, bismuth, tin, antimony, alkaline earth metal, and the like. Of all these examples, copper, and in particular, lead are preferable because hydroxyalkanal can be produced at high selectivity and yield.

Although it depends on the composition of a carboxylic-acid-based resin, an amount of metal carried by the carboxylic-acid-based resin is preferably in a range between 0.001 percent by weight and 10 percent by weight, and more preferably in a range between 0.01 percent by weight and 5 percent by weight, and most preferably in a range between 0.01 percent by weight and 1 percent by weight. A metal carrying amount less than 0.001 percent by weight is not preferable because it is insufficient to realize the effect of having the metal be carried by the resin. A metal carrying amount exceeding 10 percent by weight is not preferable either because the yield of hydroxyalkanal is reduced. Note that "carrying" referred to herein does not specify a particular form, in other words, either a salt or chelate and either an adsorption type or inclusion type will do. Also, either metal ions or metal will do. Examples of metal ions are an oxide, a halide, a sulfide, and the like.

A process of having the metal be carried by a carboxylic-acid-based resin is not especially limited, and any known method is applicable. For example, when lead is to be carried by a carboxylic-acid-based resin, the carboxylic-acid-based resin is soaked in a solution of a predetermined amount of lead compounds, such as a lead nitrate or lead acetate, and stirred under predetermined conditions to perform a cation exchange. Subsequently, the carboxylic-acid-based resin is collected by filtration or the like and rinsed with water.

The carboxylic-acid-based resin thus obtained is not necessarily dissolved uniformly in an unsaturated aldehyde solution, and the state of the carboxylic-acid-based resin in the unsaturated aldehyde is not especially limited; however, a solid carboxylic-acid-based resin is preferred. A crosslinking agent may be used in producing the carboxylic-acid-based resin, and neither an adding amount nor the kind thereof is especially limited.

The reason why a metal-carrying carboxylic-acid-based resin exhibits an excellent catalytic action in producing hydroxyalkanal out of an unsaturated aldehyde is not apparent, but the metal-carrying carboxylic-acid-based resin is assumed to curb the consecutive reaction of the reaction product, namely, hydroxyalkanal.

In case that the unsaturated aldehyde is acrolein, it is preferable to add 1,3-propanediol, which is derived from the object product, namely, 3-hydroxypropanal, to the reaction solution to obtain 3-hydroxypropanal at high selectivity and yield. An adding amount of 1,3-propanediol with respect to acrolein is preferably in a range between 0.001 percent by weight and 10 percent by weight, more preferably in a range between 0.01 percent by weight and 5 percent by weight, further preferably in a range between 0.1 percent by weight and 2 percent by weight, and most preferably about 1 percent by weight. An adding amount less than 0.001 percent by weight is not preferable because it is insufficient to realize the effect of adding 1,3-propanediol. An adding amount exceeding 10 percent by weight is not preferable either because the yield of 3-hydroxypropanal is reduced.

The reason why adding 1,3-propanediol to the reaction solution brings excellent action and effect in producing 3-hydroxypropanal out of acrolein is not apparent, but 1,3-propanediol is assumed to bond to a carboxylic-acid-based resin where the reaction takes place, so that the bonded portion will be masked to some extent, thereby curbing the consecutive reaction of the reaction product, namely, 3-hydroxypropanal.

A metal-carrying ion exchange resin is not especially limited. Any ion exchange resin which is suitable for the hydration reaction of an unsaturated aldehyde will do. Metal carried by the ion exchange resin is not especially limited either, but a preferred metal is lead. An amount of the ion exchange resin with respect to the unsaturated aldehyde is not especially limited, and it can be determined depending on the kinds of the unsaturated aldehyde and ion exchange resin, etc. A process of producing the ion exchange resin is not especially limited.

Although it depends on the composition of an ion exchange resin, an amount of metal carried by the ion exchange resin is preferably in a range between 0.001 percent by weight and 10 percent by weight, more preferably in a range between 0.01 percent by weight and 5 percent by weight, and most preferably in a range between 0.01 percent by weight and 1 percent by weight. A metal-carrying amount less than 0.001 percent by weight is not preferable because it is insufficient to realize the effect of having the metal be carried by the ion exchange resin. A metal-carrying amount exceeding 10 percent by weight is not preferable either because the yield of hydroxyalkanal is reduced.

A process of having the metal be carried by an ion exchange resin is not especially limited, and it can be done in the same manner as the metal-carrying carboxylic-acid-based resin.

The carboxylic acid added to the reaction solution in the present invention as occasion demands is not especially limited, and either a monocarboxylic acid or polycarboxylic acid will do. Examples of the carboxylic acid are: (1) a monocarboxylic acid, such as a formic acid, an acetic acid, a (meta)acrylic acid, and (2) a dicarboxylic acid, such as an oxalic acid. Of all these examples, a polycarboxylic acid, in particular, a dicarboxylic acid, such as oxalic acid, is preferable.

An adding amount of the carboxylic acid to the reaction solution with respect to the unsaturated aldehyde is, although it depends on the kinds of the unsaturated aldehyde and carboxylic acid, etc., preferably in a range between 0.01 percent by weight and 10 percent by weight, more preferably in a range between 0.01 percent by weight and 5 percent by weight, and most preferably in a range between 0.01 percent by weight and 3 percent by weight. An adding amount less than 0.01 percent by weight is not preferable because it is not sufficient to realize the effect of adding the carboxylic acid. An adding amount exceeding 10 percent by weight is not preferable either because the yield of A reaction temperature at which an unsaturated aldehyde is hydrated using a catalyst is not especially limited, but a preferable range is between 50° C. and 250° C. In case that acrolein is used as the unsaturated aldehyde, a preferable range is between 50° C. and 140° C. A reaction temperature below 50° C. is not economically preferable because a reaction rate is decreased and a hydration reaction takes a long time. A reaction temperature exceeding 250° C. is not preferable either because the unsaturated aldehyde triggers a side reaction, such as polymerization, and thus reduces the yield of hydroxyalkanal.

The present invention can be performed in a batch, semi-batch, or continuous manner, but in any case, a closed vessel is preferred for the reaction step. A reaction pressure inside the closed vessel is not especially limited, but a preferable range is between 1 kg/cm$^2$ and 20 kg/cm$^2$. In case that a reaction takes place below a boiling point of the unsaturated aldehyde, it is preferable to apply a reaction pressure in a range between 1 kg/cm$^2$ and 5 kg/cm$^2$ to the reaction vessel by taking a vaporization pressure of the unsaturated aldehyde and other ingredients into consideration. The above reaction pressure is applied, for example, by filling an inert gas($N_2$ gas, He gas, etc.) into the reaction vessel. The higher the reaction pressure, the more the unsaturated aldehyde dissolves in water and the higher the yield of hydroxyalkanal becomes. On the other hand, the anti-pressure structure of the reaction vessel must be reinforced, which increases the size of the vessel undesirably. Thus, when setting a reaction pressure, these factors must be taken into consideration.

When the reaction ends, the object product, namely, a hydroxyalkanal solution, can be readily obtained by a simple separation process, such as filtration and distillation. Further, hydroxyalkanal can be readily separated from the solution if so desired. In case of 3-hydroxyalkanal of hydroxyalkanals, it may exist in the form of a hemiacetal and an acetal in the solution, but they can be easily converted into 3-hydroxyalkanal. Likewise, hydroxyalkanal, in the presence of alcohol, may exist in the form of a hemiacetal and an acetal of the corresponding alcohol, but they can be easily converted into hydroxyalkanal.

Note that collected water, carboxylic-acid-based resin and ion exchange resin serving as a catalyst, carboxylic acid, and unreacted unsaturated aldehyde can be used repetitively for the hydration reaction.

Hereinafter, the present invention is illustrated by the following examples of a preferred embodiment in comparison with comparative examples not according to the invention. However, the present invention is not limited to the undermentioned examples. Note that a conversion of the unsaturated aldehyde expressed by Formula (I) and the selectivity of the resulting hydroxyalkanal are defined as follows:

(1) A conversion of unsaturated aldehyde (%)=(the mole number of consumed unsaturated aldehyde/the mole number of supplied unsaturated aldehyde)×100

(2) Selectivity of hydroxyalkanal (%)=(the mole number of unsaturated aldehyde converted into hydroxyalkanal/the mole number of consumed unsaturated aldehyde)×100

(3) Selectivity of dimerized hydroxyalkanal (%)=(the mole number of unsaturated aldehyde converted into dimerized hydroxyalkanal/the mole number of consumed unsaturated aldehyde)×100.

The amounts of the unsaturated aldehyde, hydroxyalkanal, and dimerized hydroxyalkanal are measured in any known manner, and gas chromatography (GC), one of known methods, is used in the present invention.

[FIRST EXAMPLE]

A predetermined amount of water is poured into a reaction vessel equipped with a thermometer, a stirring instrument, and the like, and a predetermined amount of an unsaturated aldehyde, namely, acrolein, is also poured into the reaction vessel, so that the concentration of the resulting solution is 17 percent by weight. Next, a predetermined amount of a catalyst, namely, acrylic acid-acrylamide copolymer (carboxylic-acid-based resin), is added to the solution. The amount of acrylamide in the acrylic acid-acrylamide copolymer is 5 percent by mole. The above reaction solution is subject to reaction for three hours with stirring at 80° C. to hydrate acrolein. The reaction conditions are set forth in TABLE 1 below.

When the reaction ends, the resulting reaction solution is filtered, and analyzed in a predetermined manner, the results of which are set forth below and in TABLE 2 below.

(1) conversion of acrolein: 44%

(2) selectivity of 3-hydroxypropanal: 57%

(3) selectivity of dimerized 3-hydroxypropanal: 9%

(4) selectivity of hydroxyalkanal: 66% (total of (3) and (4))

The catalyst used herein renders excellent heat resistance and can be used repetitively for the hydration reaction.

There is produced a solution containing 8.1 percent by weight of 3-hydroxypropanal and 1.3 percent by weight of dimerized 3-hydroxypropanal both obtained as the result of the above hydration reaction. A known raney nickel catalyst is added to the resulting solution to hydrogenate 3-hydroxypropanal and dimerized 3-hydroxypropanal. Reaction conditions are: a hydrogen pressure of 100 kg/cm$^2$, a reaction temperature of 60° C., and reaction time of six hours. When the reaction ends, the resulting solution is analyzed and it is acknowledged that there is produced 1,3-propanediol in an amount equal to a total of 3-hydroxypropanal and dimerized 3-hydroxypropanal. In other words, 1,3-propanediol is quantitatively produced. This indicates that dimerized 3-hydroxypropanal is converted into 1,3-propanediol by a known hydrogenation process.

[SECOND EXAMPLE]

An analysis is conducted in the same manner as the first example except that lead is carried by acrylic acid-acrylamide copolymer serving as the catalyst, 2.5 percent by weight of 1,3-propanediol with respect to acrolein is added to the reaction solution, and the reaction temperature is increased to 90° C. An amount of lead carried by the acrylic acid-acrylamide copolymer is kept equal to or lower than a predetermined level, namely, not more than 5 percent by weight. The reaction conditions are set forth in TABLE 1 below.

The results of the analysis are set forth below and TABLE 2 below.

(1) conversion of acrolein: 51%
(2) selectivity of 3-hydroxypropanal: 77%
(3) selectivity of dimerized 3-hydroxypropanal: 15%
(4) selectivity of hydroxyalkanal: 92% (total of (3) and (4))

The catalyst used herein renders excellent heat resistance and can be used repetitively for the hydration reaction.

[THIRD EXAMPLE]

An analysis is conducted in the same manner as the second example except that the density of acrolein is increased to 28 percent by weight from 17 percent by weight. The reaction conditions are set forth in TABLE 1 below.

The results of the analysis are set forth below and in TABLE 2 below.

(1) conversion of acrolein: 38%
(2) selectivity of 3-hydroxypropanal: 64%
(3) selectivity of dimerized 3-hydroxypropanal: 23%
(4) selectivity of hydroxyalkanal: 87% (total of (3) and (4))

The catalyst used herein renders excellent heat resistance and can be used repetitively for the hydration reaction.

[FOURTH EXAMPLE]

An analysis is conducted in the same manner as the third example except that the amount of acrylamide in the acrylic acid-acrylamide copolymer is increased to 20 percent by mole from 5 percent by mole. The reaction conditions are set forth in TABLE 1 below.

The results of the analysis are set forth below and in TABLE 2 below.

(1) conversion of acrolein: 56%
(2) selectivity of 3-hydroxypropanal: 67%
(3) selectivity of dimerized 3-hydroxypropanal: 12%
(4) selectivity of hydroxyalkanal: 79% (total of (3) and (4))

The catalyst used herein renders excellent heat resistance and can be used repetitively for the hydration reaction.

[FIFTH EXAMPLE]

An analysis is conducted in the same manner as the third example except that acrylic acid-N,N-dimethylacrylamide copolymer is used instead of acrylic acid-acrylamide copolymer. The amount of N,N-dimethylacrylamide in the acrylic acid-N,N-dimethylacrylamide copolymer is 5 percent by mole. The reaction conditions are set forth in TABLE 1 below.

The results of the analysis are set forth below and in TABLE 2 below.

(1) conversion of acrolein: 41%
(2) selectivity of 3-hydroxypropanal: 60%
(3) selectivity of dimerized 3-hydroxypropanal: 20%
(4) selectivity of hydroxyalkanal: 80% (total of (3) and (4))

The catalyst used herein renders excellent heat resistance and can be used repetitively for the hydration reaction.

[SIXTH EXAMPLE]

An analysis is conducted in the same manner as the third example except that acrylic acid-N-isopropylacrylamide copolymer is used instead of acrylic acid-acrylamide copolymer. The amount of N-isopropylacrylamide in the acrylic acid-N-isopropylacrylamide copolymer is 5 percent by mole. The reaction conditions are set forth in TABLE 1 below.

The results of the analysis are set forth below and in TABLE 2 below.

(1) conversion of acrolein: 42%
(2) selectivity of 3-hydroxypropanal: 57%
(3) selectivity of dimerized 3-hydroxypropanal: 19%
(4) selectivity of hydroxyalkanal: 76% (total of (3) and (4))

The catalyst used herein renders excellent heat resistance and can be used repetitively for the hydration reaction.

[SEVENTH EXAMPLE]

An analysis is conducted in the same manner as the third example except that acrylic acid-N,N-dimethylaminopropylacrylamide copolymer is used instead of acrylic acid-acrylamide copolymer. The amount of N,N-dimethylaminopropylacrylamide in the acrylic acid-N,N-dimethylaminopropylacrylamide copolymer is 5 percent by mole. The reaction conditions are set forth in TABLE 1 below.

The results of the analysis are set forth below and in TABLE 2 below.

(1) conversion of acrolein: 46%
(2) selectivity of 3-hydroxypropanal: 57%
(3) selectivity of dimerized 3-hydroxypropanal: 18%
(4) selectivity of hydroxyalkanal: 75% (total of (3) and (4))

The catalyst used herein renders excellent heat resistance and can be used repetitively for the hydration reaction.

[EIGHTH EXAMPLE]

An analysis is conducted in the same manner as the third example except that acrylic acid-N,N-diethylacrylamide copolymer is used instead of acrylic acid-acrylamide copolymer. The amount of N,N-diethylacrylamide in the acrylic acid-N,N-diethylacrylamide copolymer is 5 percent by mole. The reaction conditions are set forth in TABLE 1 below.

The results of the analysis are set forth below and in TABLE 2 below.

(1) conversion of acrolein: 58%

(2) selectivity of 3-hydroxypropanal: 65%

(3) selectivity of dimerized 3-hydroxypropanal: 12%

(4) selectivity of hydroxyalkanal: 77% (total of (3) and (4))

The catalyst used herein renders excellent heat resistance and can be used repetitively for the hydration reaction.

[NINTH EXAMPLE]

An analysis is conducted in the same manner as the first example except that acrylic acid-N,N-dimethylaminopropylacrylamide copolymer is used instead of acrylic acid-acrylamide copolymer, 1.3 percent by weight of 1,3-propanediol with respect to acrolein is added to the reaction solution, and a reaction temperature is increased to 90° C. The amount of N,N-dimethylaminopropylacrylamide in the acrylic acid-N, N-dimethylaminopropylacrylamide copolymer is 5 percent by mole. The reaction conditions are set forth in TABLE 1 below.

The results of the analysis are set forth below and in TABLE 2 below.

(1) conversion of acrolein: 30%

(2) selectivity of 3-hydroxypropanal: 64%

(3) selectivity of dimerized 3-hydroxypropanal: 16%

(4) selectivity of hydroxyalkanal: 80% (total of (3) and (4))

The catalyst used herein renders excellent heat resistance and can be used repetitively for the hydration reaction.

[TENTH EXAMPLE]

An analysis is conducted in the same manner as the first example except that acrylic acid-N-vinylpyrrolidone copolymer is used instead of acrylic acid-acrylamide copolymer, and 2.5 percent by weight of 1,3-propanediol with respect to acrolein is added to the reaction solution. The amount of N-vinylpyrrolidone in the acrylic acid-N-vinylpyrrolidone copolymer is 5 percent by mole. The reaction conditions are set forth in TABLE 1 below.

The results of the analysis are set forth below and in TABLE 2 below.

(1) conversion of acrolein: 28%

(2) selectivity of 3-hydroxypropanal: 71%

(3) selectivity of dimerized 3-hydroxypropanal: 8%

(4) selectivity of hydroxyalkanal: 79% (total of (3) and (4))

The catalyst used herein renders excellent heat resistance and can be used repetitively for the hydration reaction.

[ELEVENTH EXAMPLE]

An analysis is conducted in the same manner as the tenth example except that the density of acrolein is increased to 28 percent by weight from 17 percent by weight. The reaction conditions are set forth in TABLE 1 below.

The results of the analysis are set forth below and in TABLE 2 below.

(1) conversion of acrolein: 17%

(2) selectivity of 3-hydroxypropanal: 65%

(3) selectivity of dimerized 3-hydroxypropanal: 9%

(4) selectivity of hydroxyalkanal: 74% (total of (3) and (4))

The catalyst used herein renders excellent heat resistance and can be used repetitively for the hydration reaction.

[FIRST COMPARATIVE EXAMPLE]

An analysis is conducted in the same manner as the second example except that an aluminium-carrying ion exchange resin is used instead of the lead-carrying acrylic acid-acrylamide copolymer, the reaction temperature is lowered to 70° C., and no 1,3-propanediol is added to the reaction solution. Duolite C467, namely, "Duolite" of Rohm & Haas Co., is used as the ion exchange resin, and an amount of lead carried by the resin is kept equal to or lower than a predetermined level, namely, not more than 5 percent by weight. The reaction conditions are set forth in TABLE 1 below.

The results of the analysis are set forth below and in TABLE 2 below.

(1) conversion of acrolein: 44%

(2) selectivity of 3-hydroxypropanal: 46%

(3) selectivity of dimerized 3-hydroxypropanal: 5%

(4) selectivity of hydroxyalkanal: 51% (total of (3) and (4))

The catalyst used herein renders poor heat resistance and can not be used repetitively for the hydration reaction.

TABLE 1

| | ACROLEIN DENSITY (% WT) | CARBOXYLIC-ACID-BASED RESIN (COPOLYMER) | TEMP. (°C.) | TIME (HR) | 1,3-PROPANE-DIOL (% WT) | AMOUNT OF Pb (% WT) |
|---|---|---|---|---|---|---|
| EX. 1 | 17 | A-ACRYLAMIDE (ACRYLAMIDE 5% MOL) | 80 | 3 | — | — |
| EX. 2 | 17 | A-ACRYLAMIDE (ACRYLAMIDE 5% MOL) | 90 | 3 | 2.5 | 5 OR LESS |
| EX. 3 | 28 | A-ACRYLAMIDE (ACRYLAMIDE 5% MOL) | 90 | 3 | 2.5 | 5 OR LESS |
| EX. 4 | 28 | A-ACRYLAMIDE (ACRYLAMIDE 20% MOL) | 90 | 3 | 2.5 | 5 OR LESS |
| EX. 5 | 28 | A-N,N-DIMETHYL ACRYLAMIDE | 90 | 3 | 2.5 | 5 OR LESS |

TABLE 1-continued

| | ACROLEIN DENSITY (% WT) | CARBOXYLIC-ACID-BASED RESIN (COPOLYMER) | TEMP. (°C.) | TIME (HR) | 1,3-PROPANE-DIOL (% WT) | AMOUNT OF Pb (% WT) |
|---|---|---|---|---|---|---|
| EX. 6 | 28 | (N,N-DIMETHYL ACRYLAMIDE 5% MOL) A-N-ISOPROPYL ACRYLAMIDE (N-ISOPROPYL-ACRYLAMIDE 5% MOL) | 90 | 3 | 2.5 | 5 OR LESS |
| EX. 7 | 28 | A-N,N-DIMETHHYL AMINOPROPYL ACRYLAMIDE (N,N-DIMETHYL AMINO-PROPYLACRYLAMIDE 5% MOL) | 90 | 3 | 2.5 | 5 OR LESS |
| EX. 8 | 28 | A-N,N-DIETHYHL ACRYLAMIDE (N,N-DIETHYL-ACRYLAMIDE 5% MOL) | 90 | 3 | 2.5 | 5 OR LESS |
| EX. 9 | 17 | A-N,N-DIMETHYL-AMINOPROPYL ACRYLAMIDE (N,N-DIMETHYLAMINO-PROPYLACRYLAMIDE 5% MOL) | 90 | 3 | 1.3 | — |
| EX. 10 | 17 | 1-N-VINYL-PYRROLIDONE (N-VINYLPYRROLIDONE 5% MOL) | 80 | 3 | 2.5 | — |
| EX. 11 | 28 | A-N-VINYL-PYRROLIDONE (N-VINYLPYRROLIDONE 5% MOL) | 80 | 3 | 2.5 | — |
| COMPARATIVE EX. 1 | 17 | ION EXCHANGE RESIN | 70 | 3 | — | Al 5 OR LESS |

A represents acrylic acid

TABLE 2

| | CONVERSION OF ACROLEIN (%) | SELECTIVITY OF 3-HYDROXY-PROPANAL (%) | SELECTIVITY OF DIMERIZED 3-HYDROXY-PROPANAL (%) | SELECTIVITY OF HYDROXY-ALKANAL (%) |
|---|---|---|---|---|
| EX. 1 | 44 | 57 | 9 | 66 |
| EX. 2 | 51 | 77 | 15 | 92 |
| EX. 3 | 38 | 64 | 23 | 87 |
| EX. 4 | 56 | 67 | 12 | 79 |
| EX. 5 | 41 | 60 | 20 | 80 |
| EX. 6 | 42 | 57 | 19 | 76 |
| EX. 7 | 46 | 57 | 18 | 75 |
| EX. 8 | 58 | 65 | 12 | 77 |
| EX. 9 | 30 | 64 | 12 | 77 |
| EX. 10 | 28 | 71 | 8 | 79 |
| EX. 11 | 17 | 65 | 9 | 74 |
| COMPARATIVE EX. 1 | 44 | 46 | 5 | 51 |

[TWELFTH EXAMPLE]

A predetermined amount of water is poured into a reaction vessel equipped with a thermometer, a stirring instrument, and the like, and a predetermined amount of acrolein is also poured into the reaction vessel, so that the concentration of the resulting solution is 17 percent by weight. Also, 2.5 percent by weight of 1,3-propanediol with respect to acrolein is added to the above solution. Next, a predetermined amount of a catalyst, namely, acrylic acid-N,N-diarylamine copolymer (carboxylic-acid-based resin), is added to the solution. The amount of N,N-diarylamine in the acrylic acid-N,N-diarylamine copolymer is 5 percent by mole. The above reaction solution is subject to reaction for three hours with stirring at 80° C. to hydrate acrolein. The reaction conditions are set forth in TABLE 3 below.

When the reaction ends, the resulting reaction solution is filtered, and analyzed in a predetermined manner, the results of which are set forth below and in TABLE 4 below.

(1) conversion of acrolein: 64%

(2) selectivity of 3-hydroxypropanal: 91%

(3) selectivity of dimerized 3-hydroxypropanal: 8%

(4) selectivity of hydroxyalkanal: 99% (total of (3) and (4))

The catalyst used herein renders excellent heat resistance and can be used repetitively for the hydration reaction.

[THIRTEENTH EXAMPLE]

An analysis is conducted in the same manner as the twelfth example except that the concentration of acrolein is increased to 28 percent by weight from 17 percent by weight. The reaction conditions are set forth in TABLE 3 below.

The results of the analysis are set forth below and in TABLE 4 below.

(1) conversion of acrolein: 56%

(2) selectivity of 3-hydroxypropanal: 68%

(3) selectivity of dimerized 3-hydroxypropanal: 9%

(4) selectivity of hydroxyalkanal: 77% (total of (3) and (4))

The catalyst used herein renders excellent heat resistance and can be used repetitively for the hydration reaction.

[FOURTEENTH EXAMPLE]

An analysis is conducted in the same manner as the twelfth example except that acrylic acid-N-vinylcarbazole copolymer is used instead of acrylic acid-N,N-diarylamine copolymer. The amount of N-vinylcarbazole in the acrylic acid-N-vinylcarbazole copolymer is 5 percent by mole. The reaction conditions are set forth in TABLE 3 below.

The results of the analysis are set forth below and in TABLE 4 below.

(1) conversion of acrolein: 63%

(2) selectivity of 3-hydroxypropanal: 91%

(3) selectivity of dimerized 3-hydroxypropanal: 8%

(4) selectivity of hydroxyalkanal: 99% (total of (3) and (4))

The catalyst used herein renders excellent heat resistance and can be used repetitively for the hydration reaction.

[FIFTEENTH EXAMPLE]

An analysis is conducted in the same manner as the twelfth example except that acrylic acid-4-(N,N-dimethylamino)ethylstyrene copolymer is used instead of acrylic acid-N,N-diarylamine copolymer. The amount of 4-(N,N-dimethylamino)ethylstyrene in the acrylic acid-4-(N,N-dimethylamino)ethylstyrene copolymer is 5 percent by mole. The reaction conditions are set forth in TABLE 3 below.

The results of the analysis are set forth below and in TABLE 4 below.

(1) conversion of acrolein: 55%

(2) selectivity of 3-hydroxypropanal: 69%

(3) selectivity of dimerized 3-hydroxypropanal: 10%

(4) selectivity of hydroxyalkanal: 79% (total of (3) and (4))

[SIXTEENTH EXAMPLE]

An analysis is conducted in the same manner as the thirteenth example except that acrylic acid-N-vinylcarbazole copolymer is used instead of acrylic acid-N,N-diarylamine copolymer. The amount of N-vinylcarbazole in the acrylic acid-N-vinylcarbazole copolymer is 5 percent by mole. The reaction conditions are set forth in TABLE 3 below.

The results of the analysis are set forth below and in TABLE 4 below.

(1) conversion of acrolein: 56%

(2) selectivity of 3-hydroxypropanal: 66%

(3) selectivity of dimerized 3-hydroxypropanal: 8%

(4) selectivity of hydroxyalkanal: 74% (total of (3) and (4))

The catalyst used herein renders excellent heat resistance and can be used repetitively for the hydration reaction.

[SEVENTEENTH EXAMPLE]

An analysis is conducted in the same manner as the thirteenth example except that acrylic acid-4-(N,N-dimethylamino)ethylstyrene copolymer is used instead of acrylic acid-N,N-diarylamine copolymer. The amount of 4-(N,N-dimethylamino)ethylstyrene in the acrylic acid-4-(N,N-dimethylamino)ethylstyrene copolymer is 5 percent by mole. The reaction conditions are set forth in TABLE 3 below.

The results of the analysis are set forth below and in TABLE 4 below.

(1) conversion of acrolein: 49%

(2) selectivity of 3-hydroxypropanal: 51%

(3) selectivity of dimerized 3-hydroxypropanal: 10%

(4) selectivity of hydroxyalkanal: 61% (total of (3) and (4))

The catalyst used herein renders excellent heat resistance and can be used repetitively for the hydration reaction.

[EIGHTEENTH EXAMPLE]

An analysis is conducted in the same manner as the twelfth example except that the reaction temperature is increased to 90° C. from 80° C. The reaction conditions are set forth in TABLE 3 below.

The results of the analysis are set forth below and in TABLE 4 below.

(1) conversion of acrolein: 72%

(2) selectivity of 3-hydroxypropanal: 78%

(3) selectivity of dimerized 3-hydroxypropanal: 8%

(4) selectivity of hydroxyalkanal: 86% (total of (3) and (4))

The catalyst used herein renders excellent heat resistance and can be used repetitively for the hydration reaction.

TABLE 3

| | ACROLEIN DENSITY (% WT) | CARBOXYLIC-ACID-BASED RESIN (COPOLYMER) | TEMP. (°C.) | TIME (HR) | 1,3-PROPANE-DIOL (% WT) |
|---|---|---|---|---|---|
| EX. 12 | 17 | A-N,N-DIARYLAMINE (N,N-DIARYLAMINE 5% MOL) | 80 | 3 | 2.5 |
| EX. 13 | 28 | A-N,N-DIARYLAMINE (N,N-DIARYLAMINE 5% MOL) | 80 | 3 | 2.5 |
| EX. 14 | 17 | A-N-VINYLCARBAZOLE (N-VINYLCARBAZOLE 5% MOL) | 80 | 3 | 2.5 |
| EX. 15 | 17 | A-4-(N,N-DIMETHYL-AMINO)ETHYLSTYRENE (4-(N,N-DIMETHYLAMINO)ETHYLSTYRENE 5% MOL) | 80 | 3 | 2.5 |
| EX. 16 | 28 | A-N-VINYLCARBAZOLE (N-VINYLCARBAZOLE 5% MOL) | 80 | 3 | 2.5 |
| EX. 17 | 28 | A-4-(N,N-DIMETHYL-AMINO)ETHYLSTYRENE (4-(N,N-DIMETHYLAMINO)ETHYLSTYRENE 5% MOL) | 80 | 3 | 2.5 |
| EX. 18 | 17 | A-N,N-DIARYLAMINE (N,N-DIARYLAMINE 5% MOL) | 90 | 3 | 2.5 |
| COMPARATIVE EX. 1 | 17 | ION EXCHANGE RESIN CARRYING 5% WT OR LESS A1 | 70 | 3 | — |

A represents acrylic acid

TABLE 4

| | CONVERSION OF ACROLEIN (%) | SELECTIVITY OF 3-HYDROXY-PROPANAL (%) | SELECTIVITY OF DIMERIZED 3-HYDROXY-PROPANAL (%) | SELECTIVITY OF HYDROXY-ALKANAL (%) |
|---|---|---|---|---|
| EX. 12 | 64 | 91 | 8 | 99 |
| EX. 13 | 56 | 68 | 9 | 77 |
| EX. 14 | 63 | 91 | 8 | 99 |
| EX. 15 | 55 | 69 | 10 | 79 |
| EX. 16 | 56 | 66 | 8 | 74 |
| EX. 17 | 49 | 51 | 10 | 61 |
| EX. 18 | 72 | 78 | 8 | 86 |
| COMPARATIVE EX. 1 | 44 | 46 | 5 | 51 |

[NINETEENTH EXAMPLE]

A predetermined amount of water is poured into a reaction vessel equipped with a thermometer, a stirring instrument, and the like, and a predetermined amount of acrolein is also poured into the reaction vessel, so that the density of the resulting solution is 28 percent by weight. Also, 2.5 percent by weight of 1,3-propanediol with respect to acrolein is added to the above solution. Next, a predetermined amount of a catalyst, namely, acrylic acid-N,N-diarylamine copolymer is added to the solution. The amount of N,N-diarylamine in the acrylic acid-N,N-diarylamine copolymer is 10 percent by mole. The above reaction solution is subject to reaction for three hours with stirring at 80° C. to hydrate acrolein. The reaction conditions are set forth in TABLE 5 below.

When the reaction ends, the resulting reaction solution is filtered, and analyzed in a predetermined manner, the results of which are set forth below and in TABLE 6 below.

(1) conversion of acrolein: 60%
(2) selectivity of 3-hydroxypropanal: 69%
(3) selectivity of dimerized 3-hydroxypropanal: 9%
(4) selectivity of hydroxyalkanal: 78% (total of (3) and (4))

The catalyst used herein renders excellent heat resistance and can be used repetitively for the hydration reaction.

[TWENTIETH EXAMPLE]

An analysis is conducted in the same manner as the nineteenth example except that acrylic acid-N,N,N-triarylamine copolymer (carboxylic-acid-based resin) is used instead of acrylic acid-N,N-diarylamine copolymer. The amount of N,N,N-triarylamine in the acrylic acid-N,N,N-triarylamine copolymer is 10 percent by mole. The reaction conditions are set forth in TABLE 5 below.

The results of the analysis are set forth below and in TABLE 6 below.

(1) conversion of acrolein: 58%
(2) selectivity of 3-hydroxypropanal: 61%
(3) selectivity of dimerized 3-hydroxypropanal: 4%
(4) selectivity of hydroxyalkanal: 65% (total of (3) and (4))

The catalyst used herein renders excellent heat resistance and can be used repetitively for the hydration reaction.

[TWENTY-FIRST EXAMPLE]

An analysis is conducted in the same manner as the nineteenth example except that acrylic acid-N-monoarylamine copolymer (carboxylic-acid-based resin) is used instead of acrylic acid-N,N-diarylamine copolymer. The amount of N-monoarylamine in the acrylic acid-N-monoarylamine copolymer is 5 percent by mole. The reaction conditions are set forth in TABLE 5 below.

The results of the analysis are set forth below and in TABLE 6 below.

(1) conversion of acrolein: 57%
(2) selectivity of 3-hydroxypropanal: 62%
(3) selectivity of dimerized 3-hydroxypropanal: 12%
(4) selectivity of hydroxyalkanal: 74% (total of (3) and (4))

The catalyst used herein renders excellent heat resistance and can be used repetitively for the hydration reaction.

[TWENTY-SECOND EXAMPLE]

An analysis is conducted in the same manner as the nineteenth example except that acrylic acid-N,N-diarylamineethanethiol copolymer (carboxylic-acid-based resin) is used instead of acrylic acid-N,N-diarylamine copolymer. The amount of N,N-diarylamineethanethiol in the acrylic acid-N,N-diarylamineethanethiol copolymer is 5 percent by mole. The reaction conditions are set forth in TABLE 5 below.

The results of the analysis are set forth below and in TABLE 6 below.

(1) conversion of acrolein: 61%
(2) selectivity of 3-hydroxypropanal: 74%
(3) selectivity of dimerized 3-hydroxypropanal: 11%
(4) selectivity of hydroxyalkanal: 85% (total of (3) and (4))

The catalyst used herein renders excellent heat resistance and can be used repetitively for the hydration reaction.

[TWENTY-THIRD EXAMPLE]

An analysis is conducted in the same manner as the twenty-second example except that the amount of N,N-diarylamieethanethiol in the acrylic acid-N,N-diarylamineethaneethiol copolymer is increased to 10 percent by mole from 5 percent by mole. The reaction conditions are set forth in TABLE 5 below.

The results of the analysis are set forth below and in TABLE 6 below.

(1) conversion of acrolein: 65%
(2) selectivity of 3-hydroxypropanal 69%
(3) selectivity of dimerized 3-hydroxypropanal: 7%
(4) selectivity of hydroxyalkanal: 76% (total of (3) and (4))

The catalyst used herein renders excellent heat resistance and can be used repetitively for the hydration reaction.

[TWENTY-FOURTH EXAMPLE]

A predetermined amount of water is poured into a reaction vessel equipped with a thermometer, a stirring instrument, and the like, and a predetermined amount of acrolein is also poured into the reaction vessel, so that the concentration of the resulting solution is 28 percent by weight. Also, 2.5 percent by weight of 1,3-propanediol with respect to acrolein is added to the above solution. Next, a predetermined amount of a catalyst, namely, acrylic acid-6-(N,N-dipropenylamino)-4-thiahexanoic acid copolymer is added to the solution. The amount of 6-(N,N-dipropenylamino)-4-thiahexanoic acid in the acrylic-acid-6-(N,N-dipropenylamino)-4-thiahexanoic acid copolymer is 30 percent by mole. The above reaction solution is subject to reaction for 2.5 hours with stirring at 90° C. to hydrate acrolein. The reaction conditions are set forth in TABLE 5 below.

When the reaction ends, the resulting reaction solution is filtered, and analyzed in a predetermined manner, the results of which are set forth below and in TABLE 6 below.

(1) conversion of acrolein: 64%
(2) selectivity of 3-hydroxypropanal: 80%
(3) selectivity of dimerized 3-hydroxypropanal: 8%
(4) selectivity of hydroxyalkanal: 88% (total of (3) and (4))

The catalyst used herein renders excellent heat resistance and can be used repetitively for the hydration reaction.

TABLE 5

|  | ACROLEIN DENSITY (% WT) | CARBOXYLIC-ACID-BASED RESIN (COPOLYMER) | TEMP. (°C.) | TIME (HR) | 1,3-PROPANEDIOL (% WT) |
|---|---|---|---|---|---|
| EX. 19 | 28 | A-N,N-DIARYLAMINE (N,N-DIARYLAMINE 10% MOL) | 80 | 3 | 2.5 |
| EX. 20 | 28 | A-N,N,N-TRIARYLAMINE (N,N,N-TRIARYLAMINE 10% MOL) | 80 | 3 | 2.5 |
| EX. 21 | 28 | A-N-MONOARYLAMINE (N-MONOARYLAMINE 5% MOL) | 80 | 3 | 2.5 |
| EX. 22 | 28 | A-N,N-DIARYLAMINE-ETHANETHIOL (N,N-DIARYLAMINEETHANETHIOL 5% MOL) | 80 | 3 | 2.5 |
| EX. 23 | 28 | A-N,N-DIARYLAMINE-ETHANETHIOL (N,N-DIARYLAMINEETHANETHIOL 10% MOL) | 80 | 3 | 2.5 |
| EX. 24 | 28 | A-6-(N,N-DIPROPENYLAMINO)-4-THIAHEXANOIC ACID | 90 | 2.5 | 2.5 |

TABLE 5-continued

| ACROLEIN DENSITY (% WT) | CARBOXYLIC-ACID-BASED RESIN (COPOLYMER) | TEMP. (°C.) | TIME (HR) | 1,3-PROPANE-DIOL (% WT) |
|---|---|---|---|---|
| | (6-(N,N-DIPROPENYLAMINO)-4-THIAHEXANOIC ACID 30% MOL) | | | |

A represents acrylic acid

TABLE 6

| | CONVERSION OF ACROLEIN (%) | SELECTIVITY OF 3-HYDROXY-PROPANAL (%) | SELECTIVITY OF DIMERIZED 3-HYDROXY-PROPANAL (%) | SELECTIVITY OF HYDROXY-ALKANAL (%) |
|---|---|---|---|---|
| EX. 19 | 60 | 69 | 9 | 78 |
| EX. 20 | 58 | 61 | 4 | 65 |
| EX. 21 | 57 | 62 | 12 | 74 |
| EX. 22 | 61 | 74 | 11·1 | 85 |
| EX. 23 | 65 | 69 | 7 | 76 |
| EX. 24 | 64 | 80 | 8 | 88 |

TABLES 2, 4, and 6 reveal that using a carboxylic-acid-based resin having a nitrogen containing group as a catalyst can increase the reaction rate by heating while curbing the consecutive reaction of the reaction product, namely, 3-hydroxypropanal. Thus, 3-hydroxypropanal can be produced at high selectivity and yield out of a high-density acrolein solution. In addition, the catalyst retains excellent heat resistance and can be used repetitively.

[TWENTY-FIFTH EXAMPLE]

A predetermined amount of water is poured into a reaction vessel equipped with a thermometer, a stirring instrument, and the like, and a predetermined amount of acrolein is also poured into the reaction vessel, so that the concentration of the resulting solution is 17 percent by weight. Also, a predetermined amount of lead-carrying ion exchange resin and 2.5 percent by weight of a carboxylic acid, namely, an oxalic acid, with respect to acrolein are added to the above solution. "Duolite" of Rohm & Haas Co., is used as the ion exchange resin, and an amount of lead carried by the resin is kept equal to or lower than a predetermined level, namely, not more than 5 percent by weight.

The above reaction solution is subject to reaction for two hours with stirring at 60° C. to hydrate acrolein. When the reaction ends, the resulting reaction solution is filtered, and analyzed in a predetermined manner, the results of which are set forth below.

(1) conversion of acrolein: 53%

(2) selectivity of 3-hydroxypropanal: 85%

(3) selectivity of dimerized 3-hydroxypropanal: 13%

(4) selectivity of hydroxyalkanal: 98% (total of (3) and (4))

[TWENTY-SIXTH EXAMPLE]

An analysis is conducted in the same manner as the twenty-fifth example except that the concentration of acrolein is increased to 29 percent by weight from 17 percent by weight, and the reaction time is increased to three hours, the result of which are set forth below.

(1) conversion of acrolein: 65%

(2) selectivity of 3-hydroxypropanal: 40%

(3) selectivity of dimerized 3-hydroxypropanal: 14%

(4) selectivity of hydroxyalkanal: 54% (total of (3) and (4))

[SECOND COMPARATIVE EXAMPLE]

An analysis is conducted in the same manner as the twenty-fifth example except that a carboxylic acid, namely, an oxalic acid, is omitted, the results of which are set forth below.

(1) conversion of acrolein: 55%

(2) selectivity of 3-hydroxypropanal: 79%

(3) selectivity of dimerized 3-hydroxypropanal: 10%

(4) selectivity of hydroxyalkanal: 89% (total of (3) and (4))

Here, the conversion of acrolein is low and an abundance of products are produced as a result of the consecutive reaction of 3-hydroxypropanal.

The results of the twenty-fifth and twenty-sixth examples reveal that, when a catalyst is a lead-carrying ion exchange resin and an oxalic acid is added to the reaction solution, not only an industrially advantageous short-time conversion of acrolein can be improved, but also the consecutive reaction of the reaction product, namely, 3-hydroxypropanal, is curbed. Thus, 3-hydroxypropanal can be produced at high selectivity and yield out of a high-density acrolein solution.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A process of producing hydroxyalkanal comprising a step of hydrating an unsaturated aldehyde expressed by Formula (I) below in an aqueous solution in the presence of a carboxylic-acid-based resin having at least one structure selected from the group consisting of structures expressed by Formulas (II), (III), (IV), (V), and (VI) below:

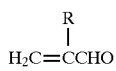

$$H_2C=\overset{\overset{R}{|}}{C}CHO \qquad (I)$$

where R represents one of a hydrogen atom and a hydrocarbon group having up to five carbons;

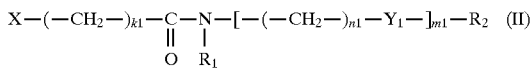

$$X-(-CH_2-)_{k1}-\overset{\overset{O}{\|}}{C}-\overset{\overset{R_1}{|}}{N}-[-(-CH_2-)_{n1}-Y_1-]_{m1}-R_2 \qquad (II)$$

where $R_1$ and $R_2$ respectively represent one of a hydrogen atom, a hydrocarbon group having up to five carbons, and a $-(-CH_2-)_{p1}-X$ group, $p_1$, $k_1$, and $m_1$ respectively represent zero or an integer of from one to six, $n_1$ represents an integer of from one to six, $Y_1$ represents one of $-O-$, $-S-$, and $-NR_3-$, $R_3$ represents one of a hydrogen atom and a hydrocarbon group having up to five carbons, and X represents a carboxylic-acid-based resin main body;

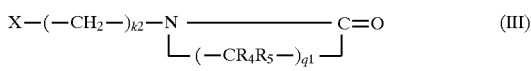

$$X-(-CH_2-)_{k2}-N\underset{\underset{(-CR_4R_5-)_{q1}}{\rule{1cm}{0.4pt}}}{\rule{1cm}{0.4pt}}C=O \qquad (III)$$

where $R_4$ and $R_5$ respectively represent one of a hydrogen atom and a hydrocarbon group having up to five carbons, $k_2$ represents zero or an integer of from one to six, $q_1$ represents an integer of from three to six, and X represents a carboxylic-acid-based resin main body;

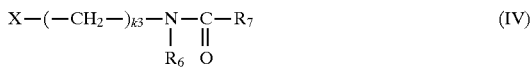

$$X-(-CH_2-)_{k3}-\overset{\overset{R_6}{|}}{N}-\overset{\overset{O}{\|}}{C}-R_7 \qquad (IV)$$

where $R_6$ represents one of a hydrogen atom, a hydrocarbon group having up to five carbons, and a $-(-CH_2-)_{p2}-X$ group, $p_2$ represents zero or an integer of from one to six, $R_7$ represents one of a hydrocarbon group having up to five carbons and a $-(-CH_2-)_{p3}-X$ group, $p_3$ and $k_3$ respectively represent zero or an integer of from one to six, and X represents a carboxylic-acid-based resin main body;

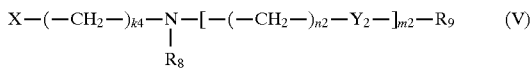

$$X-(-CH_2-)_{k4}-\overset{\overset{R_8}{|}}{N}-[-(-CH_2-)_{n2}-Y_2-]_{m2}-R_9 \qquad (V)$$

where $R_8$ represents one of a hydrogen atom, a hydrocarbon group having up to five carbons, and a $-(-CH_2-)_{p4}-X$ group, $p_4$ and $k_4$ respectively represent zero or an integer of from one to six, $n_2$ represents an integer of from one to six, $Y_2$ represents one of $-O-$, $-S-$, $-NR_{10}-$, and $-CH_2-$, $R_{10}$ represents one of a hydrogen atom and a hydrocarbon group having up to five carbons, and X represents a carboxylic-acid-based resin main body, $m_2$ represents zero or an integer of from one to six, $R_9$, when $m_2 \ne 0$, represents one of a hydrogen atom, a hydrocarbon group having up to five carbons, a $-(-CH_2-)_{p5}-X$ group, and a Brønsted acid residue and, when $m_2 \ne 0$, one of a hydrogen atom, a hydrocarbon group having up to five carbons, and a $-(-CH_2-)_{p5}-X$ group, and $p_5$ represents zero or an integer of from one to six;

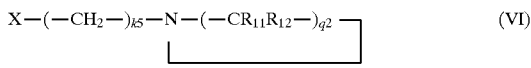

$$X-(-CH_2-)_{k5}-N-(-CR_{11}R_{12}-)_{q2}\rule{1cm}{0.4pt} \qquad (VI)$$

where $R_{11}$ and $R_{12}$ respectively represent one of a hydrogen atom and a hydrocarbon group having up to five carbons, $k_5$ represents zero or an integer of from one to six, $q_2$ represents an integer of from four to seven, and X represents a carboxylic-acid-based resin main body; wherein a ratio of the number of nitrogen containing groups to the number of carboxyl groups in said carboxylic-acid-based resin (the number of nitrogen containing groups/the number of carboxyl groups) is in a range between 1/1000 and 1/1.

2. The process of claim 1, wherein a ratio of the number of nitrogen containing groups to the number of carboxyl groups in said carboxylic-acid-based resin is in a range between 1/100 and 1/1.5.

3. The process of claim 1, wherein a ratio of the number of nitrogen containing groups to the number of carboxyl groups in said carboxylic-acid-based resin is in a range between 1/20 and 1/2.

4. The process of claim 1, wherein said carboxylic-acid-based resin carries metal.

5. The process of claim 4, wherein said metal is at least one metal material selected from a group consisting of copper, lead, nickel, zinc, iron, cobalt, bismuth, tin, antimony, and alkaline earth metal.

6. The process of claim 4, wherein said metal is lead.

7. The process of claim 1, wherein an amount of metal carried by said carboxylic-acid-based resin is in a range between 0.001 percent by weight and 10 percent by weight.

8. The process of claim 1, wherein an amount of metal carried by said carboxylic-acid-based resin is in a range between 0.01 percent by weight and 5 percent by weight.

9. The process of claim 1, wherein an amount of metal carried by said carboxylic-acid-based resin is in a range between 0.01 percent by weight and 1 percent by weight.

10. The process of claim 1, wherein said carboxylic-acid-based resin is a (meta)acrylic-acid-based resin.

11. The process of claim 10, wherein said (meta)acrylic-acid-based resin is at least one material selected from a group consisting of a (meta)acrylic acid-(meta)acrylamides copolymer and a (meta)acrylic acid-vinylpyrolidones copolymer.

12. The process of claim 1, wherein said step is carried out at a temperature in a range between 50° C. and 250° C.

13. The process of claim 1, wherein said step is carried out under a pressure in a range between 1 kg/cm$^2$ and 20 kg/cm$^2$.

14. The process of claim 1, wherein said step is carried out under a pressure in a range between 1 kg/cm$^2$ and 5 kg/cm$^2$.

15. The process of claim 1, wherein a concentration of the unsaturated aldehyde solution is in a range between 5 percent by weight and saturation.

16. The process of claim 1, wherein a concentration of the unsaturated aldehyde solution is in a range between 5 percent by weight and 50 percent by weight.

17. The process of claim 1, wherein a concentration of the unsaturated aldehyde solution is in a range between 20 percent by weight and 50 percent by weight.

18. The process of claim 1, wherein a concentration of the unsaturated aldehyde solution is in a range between 25 percent by weight and 40 percent by weight.

19. The process of claim 1, wherein said unsaturated aldehyde is at least one material selected from a group consisting of acrolein, methacrolein, 2-formyl-1-butene, 2-formyl-1-pentene, 2-formyl-1-hexene, and 2-formyl-1-heptene.

20. The process of claim 1, wherein said unsaturated aldehyde is acrolein.

21. The process of claim 20, wherein said step is carried out at a temperature in a range between 50° C. and 140° C.

22. The process of claim 20 further comprising a step of adding 1,3-propanediol to the reaction solution, said step being carried out before the step of hydrating the unsaturated aldehyde.

23. The process of claim 22, wherein an amount of said 1,3-propanediol added to the reaction solution is in a range between 0.001 percent by weight and 10 percent by weight with respect to acrolein.

24. The process of claim 22, wherein an amount of said 1,3-propanediol added to the reaction solution is in a range between 0.01 percent by weight and 5 percent by weight with respect to acrolein.

25. The process of claim 22, wherein an amount of said 1,3-propanediol added to the reaction solution is in a range between 0.1 percent by weight and 2 percent by weight with respect to acrolein.

26. The process of claim 22, wherein an amount of said 1,3-propanediol added to the reaction solution is 1 percent by weight with respect to acrolein.

27. A process of producing hydroxyalkanal comprising a step of hydrating an unsaturated aldehyde expressed by Formula (I) below in an aqueous solution in the presence of a carboxylic-acid-based resin made of a copolymer of an unsaturated monomer (A) containing a carboxyl group with an unsaturated monomer (B) containing an amino group and/or an amide group:

where R represents one of a hydrogen atom and a hydrocarbon group having up to five carbons and wherein the number of nitrogen containing groups to the number of carboxyl groups in said carboxylic-acid-based resin (the number of nitrogen containing groups/the number of carboxyl groups) is in a range between 1/1000 and 1/1.

28. The process of claim 27, wherein a substitutional group expressed by Formula (VII) below bonds to a nitrogen atom forming the amino group and/or amide group of said unsaturated monomer (B):

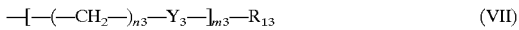

where $n_3$ represents an integer from one to six, $Y_3$ represents one of —O—, —S—, —$NR_{14}$—, and —$CH_2$—, $R_{14}$ represents one of a hydrogen atom and a hydrocarbon having up to five carbons, $m_3$ represents an integer from zero to six, $R_{13}$, when $m_3 \neq 0$, represents one of a hydrogen atom, a hydrocarbon group having up to five carbons and Brbnsted acid residue and, when m=0, one of a hydrogen atom and a hydrocarbon group having up to five carbons.

29. The process of claim 27, wherein said unsaturated monomer (B) is at least one nitrogen-containing unsaturated compound selected from a group consisting of vinylpyridines, N-vinylcarbazoles, N-monoarylamines, N,N-diarylamines, N,N,N-triarylamines, 4-(N,N-dialkylamino)alkylstyrenes, 6-(N-propenylamino)-4-thiahexanoic acid, and 6-(N,N-dipropenylamino)-4-thiahexanoic acid.

30. The process of claim 27, wherein a ratio of the number of nitrogen containing groups to the number of carboxyl groups in said carboxylic-acid-based resin is in a range between 1/100 and 1/1.5.

31. The process of claim 27, wherein a ratio of the number of nitrogen containing groups to the number of carboxyl groups in said carboxylic-acid-based resin is in a range between 1/20 and 1/2.

32. The process of claim 27, wherein said carboxylic-acid-based resin carries metal.

33. The process of claim 32, wherein said metal is at least one metal material selected from a group consisting of copper, lead, nickel, zinc, iron, cobalt, bismuth, tin, antimony, and alkaline earth metal.

34. The process of claim 32, wherein said metal is lead.

35. The process of claim 27, wherein an amount of metal carried by said carboxylic-acid-based resin is in a range between 0.001 percent by weight and 10 percent by weight.

36. The process of claim 27, wherein an amount of metal carried by said carboxylic-acid-based resin is in a range between 0.01 percent by weight and 5 percent by weight.

37. The process of claim 27, wherein an amount of metal carried by said carboxylic-acid-based resin is in a range between 0.01 percent by weight and 1 percent by weight.

38. The process of claim 27, wherein said carboxylic-acid-based resin is a (meta)acrylic-acid-based resin.

39. The process of claim 27, wherein said step is carried out at a temperature in a range between 50° C. and 250° C.

40. The process of claim 27, wherein said step is carried out under a pressure in a range between 1 kg/cm² and 20 kg/cm².

41. The process of claim 27, wherein said step is carried out under a pressure in a range between 1 kg/cm² and 5 kg/cm².

42. The process of claim 27, wherein a concentration of the unsaturated aldehyde solution is in a range between 5 percent by weight and saturation.

43. The process of claim 27, wherein a concentration of the unsaturated aldehyde solution is in a range between 5 percent by weight and 50 percent by weight.

44. The process of claim 27, wherein a concentration of the unsaturated aldehyde solution is in a range between 20 percent by weight and 50 percent by weight.

45. The process of claim 27, wherein a concentration of the unsaturated aldehyde solution is in a range between 25 percent by weight and 40 percent by weight.

46. The process of claim 27, wherein said unsaturated aldehyde is at least one material selected from a group consisting of acrolein, methacrolein, 2-formyl-1-butene, 2-formyl-1-pentene, 2-formyl-1-hexene, and 2-formyl-1-heptene.

47. The process of claim 27, wherein said unsaturated aldehyde is acrolein.

48. The process of claim 47, wherein said step is carried out at a temperature in a range between 50° C. and 140° C.

49. The process of claim 47 further comprising a step of adding 1,3-propanediol to the reaction solution, said step being carried out before the step of hydrating the unsaturated aldehyde.

50. The process of claim 47, wherein an amount of said 1,3-propanediol added to the reaction solution is in a range between 0.001 percent by weight and 10 percent by weight with respect to acrolein.

51. The process of claim 47, wherein an amount of said 1,3-propanediol added to the reaction solution is in a range between 0.01 percent by weight and 5 percent by weight with respect to acrolein.

52. The process of claim 47, wherein an amount of said 1,3-propanediol added to the reaction solution is in a range between 0.1 percent by weight and 2 percent by weight with respect to acrolein.

53. The process of claim 47, wherein an amount of said 1,3-propanediol added to the reaction solution is 1 percent by weight with respect to acrolein.

54. A process of producing a hydroxyalkanal comprising a step of hydrating an unsaturated aldehyde expressed by Formula (I) below in an aqueous solution in the presence of a metal-carrying ion exchange resin:

where R represents one of a hydrogen atom and a hydrocarbon group having up to five carbons; wherein said step is carried out at a temperature in a range between 50° C. and 250° C. and a pressure in a range between 1 kg/cm² and 20 kg/cm², wherein the concentration of the unsaturated aldehyde solution is in a range between 5 percent by weight and saturation and wherein an amount of metal carried by said ion exchange resin is in a range between 0.001 percent by weight and 10 percent by weight.

55. The process of claim 54, wherein an amount of metal carried by said ion exchange resin is in a range between 0.01 percent by weight and 5 percent by weight.

56. The process of claim 54, wherein an amount of metal carried by said ion exchange resin is in a range between 0.01 percent by weight and 1 percent by weight.

57. The process of claim 54, wherein said metal is lead.

* * * * *